(12) United States Patent
Friske

(10) Patent No.: US 8,945,076 B2
(45) Date of Patent: Feb. 3, 2015

(54) OSTOMY APPLIANCE WITH INTEGRATED BELT TABS

(75) Inventor: Timothy A. Friske, Round Lake Beach, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 13/553,357

(22) Filed: Jul. 19, 2012

(65) Prior Publication Data

US 2013/0035654 A1 Feb. 7, 2013

Related U.S. Application Data

(60) Provisional application No. 61/514,536, filed on Aug. 3, 2011.

(51) Int. Cl.
*A61F 5/44* (2006.01)
*A61F 5/445* (2006.01)
*A61F 5/449* (2006.01)

(52) U.S. Cl.
CPC ............... *A61F 5/445* (2013.01); *A61F 5/449* (2013.01)
USPC ........................................ 604/344; 604/339

(58) Field of Classification Search
CPC ..................................................... A61F 5/449
USPC ......................................... 604/344, 339, 343
See application file for complete search history.

(56) References Cited

U.S. PATENT DOCUMENTS

| | | | |
|---|---|---|---|
| 2,294,537 A * | 9/1942 | Carhart | 604/339 |
| 2,503,056 A | 4/1950 | Lay | |
| 2,759,477 A * | 8/1956 | Mains | 604/343 |
| 2,788,785 A | 4/1957 | Present | |
| 3,351,061 A * | 11/1967 | Nolan | 604/336 |
| 3,352,737 A * | 11/1967 | Jordan | 156/514 |
| 3,712,304 A * | 1/1973 | Marsan | 604/336 |
| 3,805,789 A | 4/1974 | Marsan | |
| 3,869,762 A | 3/1975 | Barrett et al. | |
| 3,898,990 A * | 8/1975 | Nolan | 604/336 |
| 4,078,568 A * | 3/1978 | Etes et al. | 604/336 |
| 4,203,445 A * | 5/1980 | Jessup et al. | 604/333 |
| 4,213,458 A | 7/1980 | Nolan et al. | |

(Continued)

FOREIGN PATENT DOCUMENTS

JP     3109779 U     4/2005

OTHER PUBLICATIONS

Brochure for Marlen's New Ultra One Piece Convex Disposable System.

(Continued)

*Primary Examiner* — Susan Su
*Assistant Examiner* — Guy K Townsend
(74) *Attorney, Agent, or Firm* — Levenfeld Pearlstein, LLC

(57) ABSTRACT

A one-piece ostomy appliance adapted to be removably attached to a patient for receiving discharge from a stoma of the patient includes a pouch that defines a cavity. A first opening is defined by the pouch for receiving a stoma and communicating discharge from the stoma into the cavity. The ostomy appliance also includes a face plate having a first side secured to the pouch and a second opposing side that includes an adhesive for securing the pouch to a patient. A second opening is defined by the face plate and is generally aligned with the first opening. Further, the ostomy appliance includes one or more tabs for coupling a belt thereto, wherein the one or more tabs are coupled directly to the face plate.

18 Claims, 2 Drawing Sheets

(56) References Cited

U.S. PATENT DOCUMENTS

| | | | |
|---|---|---|---|
| 4,219,023 A | 8/1980 | Galindo | |
| 4,274,848 A * | 6/1981 | La Gro | 96/6 |
| 4,280,498 A | 7/1981 | Jensen | |
| 4,326,521 A * | 4/1982 | Marsan | 604/342 |
| 4,411,659 A * | 10/1983 | Jensen et al. | 604/332 |
| 4,419,100 A * | 12/1983 | Alexander | 604/339 |
| 4,610,676 A * | 9/1986 | Schneider et al. | 604/339 |
| 4,642,107 A * | 2/1987 | Arnone et al. | 604/342 |
| 4,710,182 A | 12/1987 | Bryson | |
| 4,850,985 A * | 7/1989 | Edwards et al. | 604/339 |
| 4,925,216 A | 5/1990 | Steer | |
| 5,013,307 A * | 5/1991 | Broida | 604/338 |
| 5,180,377 A | 1/1993 | Holtermann | |
| 5,195,996 A | 3/1993 | Edwards et al. | |
| 5,203,806 A * | 4/1993 | Broida | 604/338 |
| 5,312,381 A * | 5/1994 | Brooks | 604/338 |
| 5,330,454 A * | 7/1994 | Klingler et al. | 604/338 |
| 5,423,783 A * | 6/1995 | Battles et al. | 604/344 |
| 5,429,626 A * | 7/1995 | Fenton | 604/339 |
| 5,618,276 A | 4/1997 | Leise, Jr. et al. | |
| 5,626,570 A | 5/1997 | Gallo | |
| 5,629,079 A * | 5/1997 | Battles et al. | 442/60 |
| 5,662,628 A * | 9/1997 | Hollands | 604/342 |
| 5,693,036 A | 12/1997 | Kilgour | |
| 5,709,674 A | 1/1998 | Steer | |
| 5,843,053 A | 12/1998 | Steer | |
| 5,938,647 A | 8/1999 | Smith | |
| 5,947,941 A * | 9/1999 | Leise et al. | 604/338 |
| 6,106,507 A | 8/2000 | Botten et al. | |
| 6,197,010 B1 * | 3/2001 | Leise et al. | 604/338 |
| 6,537,261 B1 * | 3/2003 | Steer et al. | 604/342 |
| 6,869,422 B2 | 3/2005 | Fenton | |
| 7,166,091 B1 | 1/2007 | Zeltner | |
| 7,416,543 B2 | 8/2008 | Brown et al. | |
| 7,540,861 B1 | 6/2009 | Voto | |
| 7,604,622 B2 | 10/2009 | Pedersen et al. | |
| 7,879,016 B2 | 2/2011 | Mandzij et al. | |
| 2005/0256466 A1 | 11/2005 | Winkler | |
| 2006/0015079 A1 * | 1/2006 | Mandzij et al. | 604/317 |
| 2006/0253090 A1 * | 11/2006 | Bradley et al. | 604/334 |
| 2007/0282271 A1 * | 12/2007 | Kaplan et al. | 604/174 |
| 2008/0269699 A1 | 10/2008 | O'Toole | |
| 2008/0269700 A1 | 10/2008 | O'Toole et al. | |
| 2008/0294129 A1 * | 11/2008 | Giori et al. | 604/332 |
| 2009/0234312 A1 | 9/2009 | O'Toole et al. | |
| 2009/0299309 A1 * | 12/2009 | Fenton | 604/336 |

OTHER PUBLICATIONS

European Search Report issued in connection with EP 12177420 on Oct. 31, 2012.

* cited by examiner

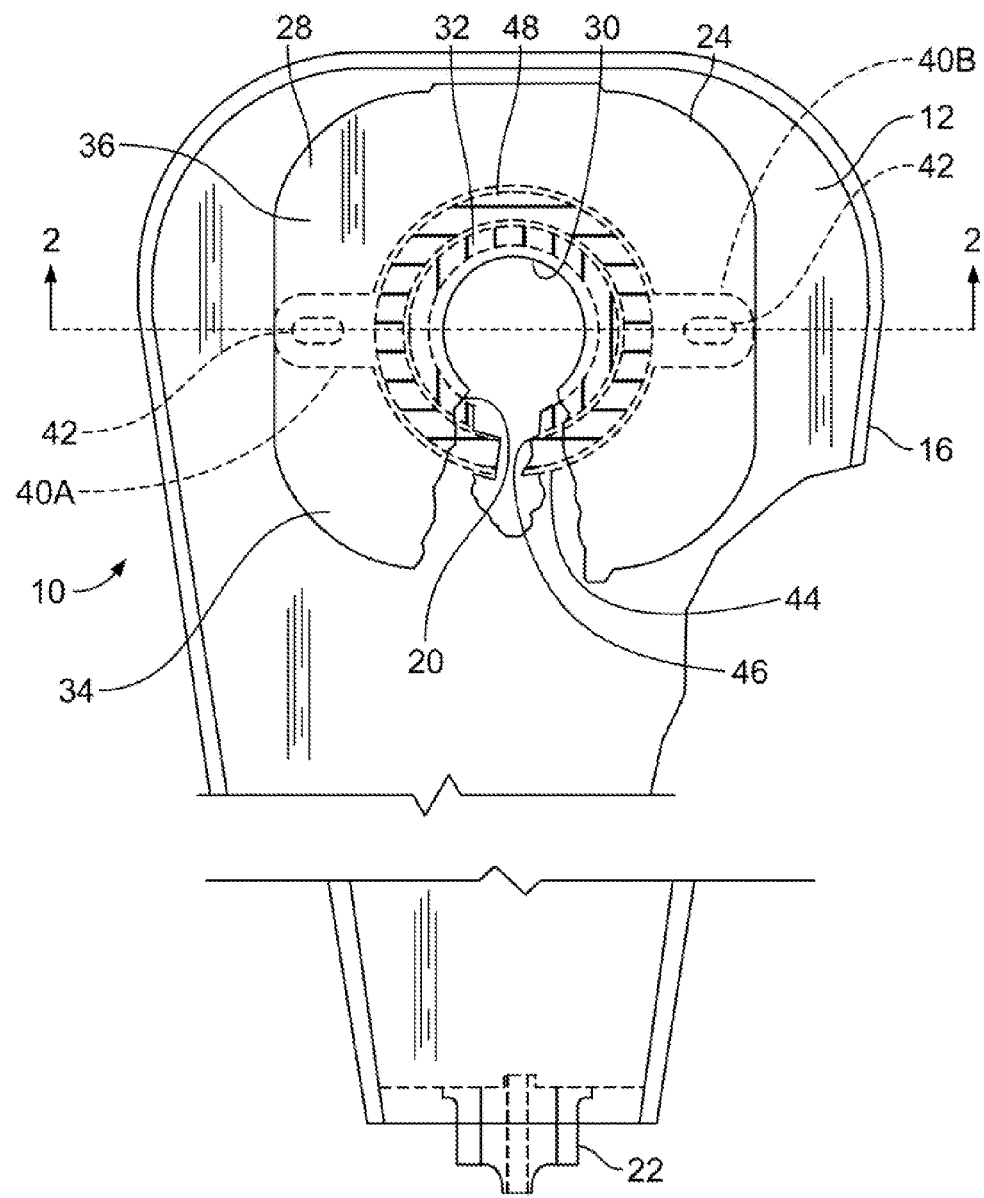
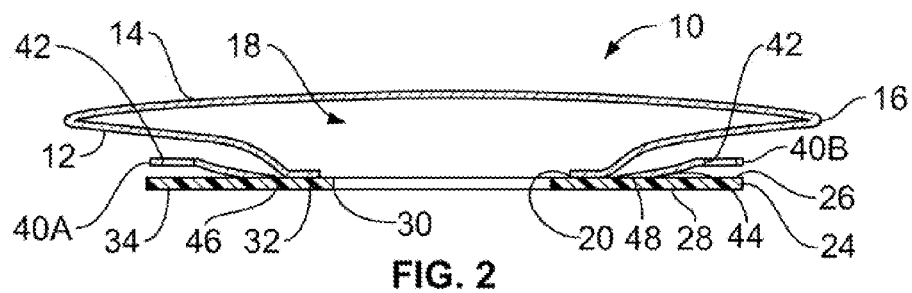

OSTOMY APPLIANCE WITH INTEGRATED BELT TABS

BACKGROUND

Ostomy appliances for receiving body waste material, such as ostomy pouches, are known. Such pouches may be used, for example by people who have had surgery such as colostomy, ileostomy, or urostomy, and typically include opposing sidewalls of flexible polymer film material that are sealed along peripheral edges thereof to define a cavity between the sealed sidewalls. An opening in one of the sidewalls is adapted to receive a stoma of a patient, from which waste material exits the patient and is collected in the pouch cavity. Some known ostomy appliances include a barrier ring coupled to one of the sidewalls of the pouch adjacent the opening in the sidewall. The barrier ring may include an adhesive layer for securing the pouch to the patient. Additionally, the ostomy appliance may include other securing or attachment mechanisms, such as one or more belt tabs that allow the pouch to be secured to the patient by a belt, for example. These belt tabs are typically provided on a ring made, for example, from polyethylene, that is heat sealed or otherwise attached to the pouch sidewall.

Such general examples of known pouches have proved to be effective, although, patients and health care professionals have occasionally observed that such pouches may be overly stiff and inflexible. Consequently, improvements to known pouches can be made to provide a flexible barrier ring that provides leak protection when secured to a patient. Improved pouches may also provide additional securing mechanisms, such as belt tabs, the incorporation of which should generally not detract from the flexibility and comfort of the pouches during use. In addition, such pouches may be one-piece systems to provide further leak protection.

SUMMARY

Various embodiments of the present disclosure provide a one-piece ostomy appliance adapted to be removably attached to a patient for receiving discharge from a stoma of the patient. The ostomy appliance includes a pouch that defines a cavity and a first opening defined by the pouch is configured to receive a stoma and to communicate discharge from the stoma into the cavity. The ostomy appliance also includes a face plate having a first side secured to the pouch and a second opposing side that includes an adhesive for securing the pouch to a patient. A second opening is defined by the face plate and is generally aligned with the first opening. Further, the ostomy appliance includes one or more tabs for coupling a belt thereto, wherein the one or more tabs are coupled directly to the face plate.

Other embodiments of the present disclosure provide a one-piece ostomy appliance adapted to be removably attached to a patient for receiving discharge from a stoma of the patient. The ostomy appliance includes a pouch that defines a cavity and a first opening defined by the pouch is configured to receive a stoma and to communicate discharge from the stoma into the cavity. The ostomy appliance also includes a face plate having a first side and a second opposing side, wherein the first side is secured to the pouch. Further, the ostomy appliance includes a second opening defined by the face plate and generally aligned with the first opening and one or more tabs for coupling a belt thereto. The one or more tabs are coupled directly to the face plate without being attached directly to the pouch.

In this manner, the present disclosure provides an improved one-piece pouch with a flexible barrier ring and one or more integral belt tabs.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIG. 1 is partial plan view of a pouch in accordance with an embodiment of the present disclosure;

FIG. 2 is a cross-sectional view of the pouch of FIG. 1 taken generally along lines 2-2 of FIG. 1.

DETAILED DESCRIPTION

Figure 3:
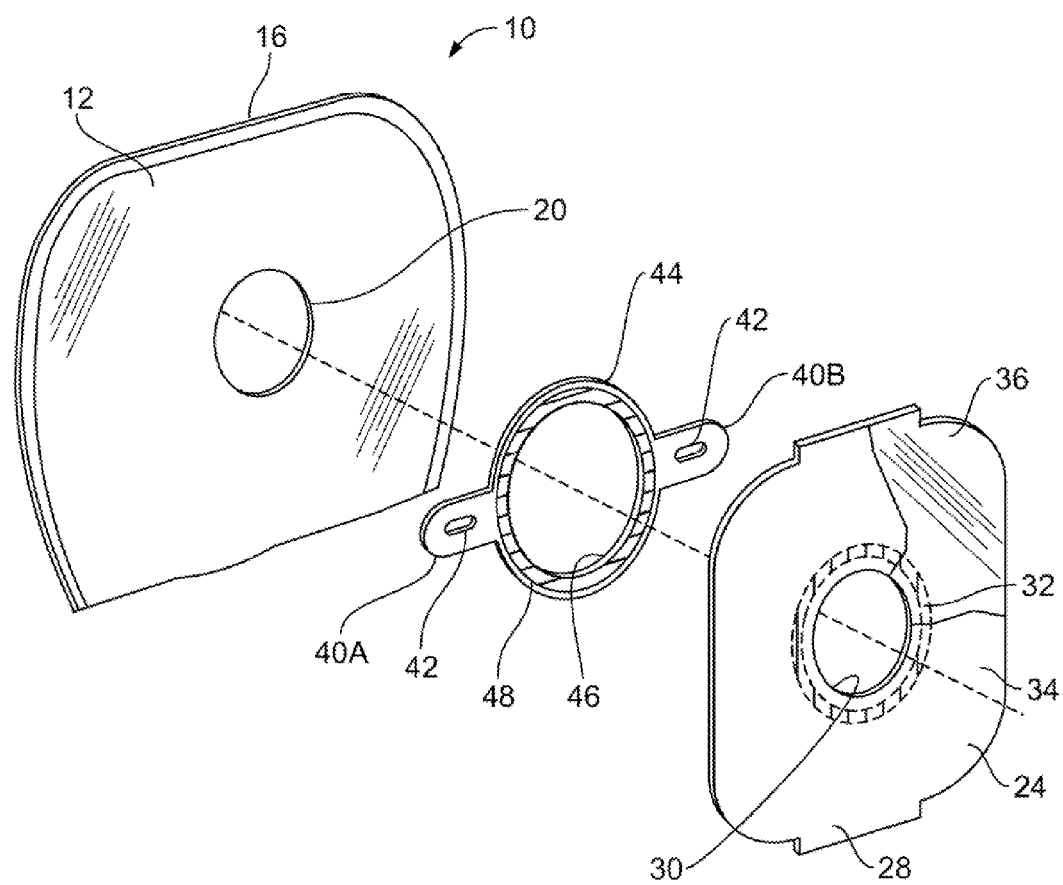
FIG. 3 is a partial exploded perspective view of the pouch of FIG. 1.

While the present device is susceptible of embodiment in various forms, there is shown in the drawings and will hereinafter be described one or more embodiments with the understanding that the present disclosure is to be considered illustrative only and is not intended to limit the device to any specific embodiment described or illustrated. The words "a" or "an" are to be taken to include both the singular and the plural. Conversely, any reference to plural items shall, where appropriate, include the singular.

Referring to FIGS. 1-3, a pouch 10 is disclosed that includes first and second opposing sidewalls 12, 14, respectively. The first and second sidewalls 12, 14 are sealed around peripheral edges 16 thereof by heat sealing or by any other suitable means to define a cavity 18 therebetween. The sidewalls 12, 14 can be formed from any suitable material, such as a flexible polymer film that is impermeable to liquids, gasses, and odors. In one example, the sidewalls 12, 14 are formed from a multilayer film. In another example, the sidewalls 12, 14 are about 4-20 mils in thickness.

In the illustrated pouch 10, an aperture or opening 20 is disposed through the first sidewall 12. The aperture 20 is illustrated as having a circular shape, although, in other examples, the aperture can be any suitable symmetric or abstract shape. The pouch 10 also includes a closure valve or assembly 22 at a lower portion thereof, which allows for the selective drainage of the contents of the pouch. Various examples of closure means are disclosed, for example, in Jensen U.S. Pat. No. 4,280,498 and Mandzij et al. U.S. Pat. No. 7,879,016, each of which are incorporated herein in its entirety. Alternatively, the closure means 22 may be omitted and the pouch 10 may be of a non-drainable or closed type.

The pouch 10 further includes a face plate or barrier 24 that has a first side 26 adjacent the first sidewall 12 of the pouch and a second side 28 facing away from the pouch. The first side 26 of the face plate 24 may include a backing film (e.g., a heat-sealable film such as EMA or EVA), and is attached to the first sidewall 12 of the pouch 10, such as by a heat seal, adhesive, or other known means. The face plate 24 further includes an aperture or opening 30 that extends therethrough. The opening 30 through the face plate 24 is generally axially aligned with the opening 20 through the first sidewall 12 of the pouch 10. In the present example, the first side 26 of the face plate 24 is attached to the first sidewall 12 of the pouch 10 in an annularly shaped area around the opening 30 in the face plate indicated generally at 32 of FIGS. 1-3, for example. Further, the opening 30 through the face plate 24 may be the same or different size and/or shape than the opening 20 through the first sidewall 12 of the pouch 10. In one example, the opening 30 is smaller than the opening 20, although the opening 30 can be cut or otherwise increased in size to accommodate stomas of different shapes and sizes.

The face plate 24 may generally be made from one or more layers of any suitable thin, flexible, and/or breathable material, such as a soft breathable material (e.g., a nonwoven material) or a non-breathable material (e.g., a thermoplastic or ethylene vinyl acetate ("EVA") film). In one example, the face plate 24 is made from a polyethylene material, which facilitates heat sealing of the face plate directly to the first sidewall 12 of pouch 10.

Further, the illustrated pouch 10 includes an adhesive layer 34 disposed over the second side 28 of the face plate 24 and a carrier or release sheet 36 disposed over the adhesive layer. The release sheet 36 can be peeled from the face plate 24 to expose the adhesive layer 34 during use so that the adhesive layer can function to adhere or secure the face plate and, thus, the pouch 10 to a patient. In one example, the release sheet 36 can be a silicon treated sheet of material to facilitate separation from the adhesive layer 34. The adhesive layer 34 may be formed from any suitable adhesive, such as known pressure-sensitive adhesives commonly used to secure face plates to skin surfaces of a patient. For example, the adhesive layer 34 may be a hypoallergenic medical-grade acrylic adhesive or a hydrocolloid-containing adhesive material capable of absorbing moisture and having both wet and dry tack. Pedersen et al. U.S. Pat. No. 7,604,622 is incorporated herein by reference and discloses additional adhesives that are suitable for use with the present pouch 10.

The pouch 10 further includes one or more tabs that allow the pouch to be secured to a patient by a belt or other similar mechanism. In the present example, the pouch 10 includes first and second tabs 40A, 40B, respectively, that each includes an opening 42 extending therethrough. The tabs 40 are attached to the first side 26 of the face plate 24 by a heat seal, adhesive, or other known means. The tabs 40 illustrated in FIGS. 1-3 extend outwardly from a belt tab ring 44, which defines a generally circular opening or aperture 46 therethrough. The opening 46 through the belt tab ring 44 is generally axially aligned with the opening 30 through the face plate 24 and the opening 20 through first sidewall 12 of the pouch 10. In the present example, the belt tab ring 44 is attached to the first side 26 of the face plate 24 in an annularly shaped area around the opening 30 in the belt tab ring 44 indicated generally at 48 of FIGS. 1-3, for example. The tabs 40 and the belt tab ring 44 are relatively thin and may be formed from a thermoplastic material. In other examples, the tabs 40 may be sealed directly to the face plate 24 and the belt tab ring 44 omitted. In one embodiment, the tabs 40 are diametrically (about 180 degrees) opposed to one another on opposite sides of the ring 44.

As seen more clearly in FIGS. 1 and 2, the area 32 where the face plate 24 is attached to the pouch 10 has a smaller circumference than the area 48 were the belt tab ring 44 is attached to the face plate 24, such that the areas of attachment do not overlap. Thus, the belt tab ring 44 is attached directly to the face plate 24 and the face plate 24 is attached directly to the pouch 10 without the belt tab ring 44 being attached directly to the pouch. This configuration has been found to provide a pouch 10 with an integral belt tab(s) 40 and face plate 24 that is convenient for a patient to wear while retaining the flexibility of the face plate. Moreover, such a configuration assures that the integrity of the seal between the patient and face plate 24 is not compromised.

Numerous modifications to the present disclosure will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A one-piece ostomy appliance adapted to be removably attached to a patient for receiving discharge from a stoma of the patient, comprising:
   a pouch that defines a cavity;
   a first opening defined by the pouch for receiving a stoma and communicating discharge from the stoma into the cavity;
   a flexible face plate having a first side secured to the pouch and a second opposing side that includes an adhesive for securing the pouch to a patient, the flexible face plate formed from one or more layers of a thin flexible polymeric material;
   a second opening defined by the face plate and generally aligned with the first opening; and
   one or more tabs for coupling a belt thereto, wherein the one or more tabs are coupled directly to the face plate, wherein the first side of the face plate is secured to the pouch by a seal in a generally annularly shaped area, and the one or more tabs are attached to the first side of the face plate outside of the annularly shaped area such that the one or more tabs are attached on the first side between the annularly shaped area and outer peripheral edges of the face plate, such that the one or more tabs and the pouch are attached separately and apart from each other on the same surface of the flexible face plate, wherein any structure that is integrally formed with the one or more tabs is not directly attached to the pouch, wherein the one or more tabs are arranged between the flexible face plate and the pouch, and wherein the flexible face plate with the one or more tabs attached thereon maintains the flexibility of the face plate.

2. The one-piece ostomy appliance of claim 1, wherein the pouch further includes first and second opposing sidewalls that are sealed to each other along peripheral edges thereof, and wherein the first opening extends through the first sidewall.

3. The one-piece ostomy appliance of claim 1, wherein the pouch is formed from a flexible film that is impermeable to liquids, gasses, and odors.

4. The one-piece ostomy appliance of claim 1, wherein the adhesive is a skin friendly adhesive material, and wherein the face plate further includes release paper disposed over the adhesive.

5. The one-piece ostomy appliance of claim 1, further comprising a closure assembly coupled to the pouch to allow drainage of the contents thereof.

6. The one-piece ostomy appliance of claim 1, wherein the first and second openings are circular openings and the second opening is smaller than the first opening.

7. The one-piece ostomy appliance of claim 1, further comprising first and second generally opposing tabs for coupling a belt thereto, wherein the first and second tabs extend outwardly from a belt tab ring that defines a third opening therethrough, wherein the third opening is generally aligned with the first and second openings.

8. The one-piece ostomy appliance of claim 7, wherein the first side of the face plate is secured to the pouch in a first generally annularly shaped area and the belt tab ring is coupled to the first side of the face plate in a second generally annularly shaped area, wherein the first generally annularly shaped area has a smaller circumference than the second generally annularly shaped area.

9. The one-piece ostomy appliance of claim 7, wherein the first and second tabs are disposed diametrically opposed to one another on opposite sides of the belt tab ring.

10. A one-piece ostomy appliance adapted to be removably attached to a patient for receiving discharge from a stoma of the patient, comprising:
   a pouch that defines a cavity;
   a first opening defined by the pouch for receiving a stoma and communicating discharge from the stoma into the cavity;
   a flexible face plate having a first side and a second opposing side, wherein the first side is secured to the pouch, the flexible face plate formed from one or more layers of a thin flexible polymeric material;
   a second opening defined by the face plate and generally aligned with the first opening; and
   one or more tabs for coupling a belt thereto, wherein the one or more tabs are coupled directly to the face plate without being attached directly to the pouch, wherein the first side of the face plate is secured to the pouch by a seal in a generally annularly shaped area, and the one or more tabs are attached to the first side of the face plate outside of the annularly shaped area such that the one or more tabs are attached on the first side between the annularly shaped area and outer peripheral edges of the face plate, such that the one or more tabs and the pouch are attached separately and apart from each other on the same surface of the flexible face plate, wherein any structure that is integrally formed with the one or more tabs is not directly attached to the pouch, wherein the one or more tabs are arranged between the flexible face plate and the pouch, and wherein the flexible face plate with the one or more tabs attached thereon maintains the flexibility of the face plate.

11. The one-piece ostomy appliance of claim 10, wherein the pouch further includes first and second opposing sidewalls that are sealed to each other along peripheral edges thereof, and wherein the first opening extends through the first sidewall.

12. The one-piece ostomy appliance of claim 10, wherein the pouch is formed from a flexible film that is impermeable to liquids, gasses, and odors.

13. The one-piece ostomy appliance of claim 10, further comprising an adhesive disposed on the second side of the face plate and a release paper disposed over the adhesive, wherein the adhesive is a skin friendly adhesive material.

14. The one-piece ostomy appliance of claim 10, further comprising a closure assembly coupled to the pouch to allow drainage of the contents thereof.

15. The one-piece ostomy appliance of claim 10, wherein the first and second openings are circular openings and the second opening is smaller than the first opening.

16. The one-piece ostomy appliance of claim 10, further comprising first and second generally opposing tabs for coupling a belt thereto, wherein the first and second tabs extend outwardly from a belt tab ring that defines a third opening therethrough, wherein the third opening is generally aligned with the first and second openings.

17. The one-piece ostomy appliance of claim 16, wherein the first side of the face plate is secured to the pouch in a first generally annularly shaped area and the belt tab ring is coupled to the first side of the face plate in a second generally annularly shaped area, wherein the first generally annularly shaped area has a smaller circumference than the second generally annularly shaped area.

18. The one-piece ostomy appliance of claim 16, wherein the first and second tabs are disposed diametrically opposed to one another on opposite sides of the belt tab ring.

* * * * *